(12) United States Patent
Mamiya

(10) Patent No.: US 11,980,770 B2
(45) Date of Patent: May 14, 2024

(54) PHOTOTHERAPY METHOD

(71) Applicant: OLYMPUS CORPORATION, Tokyo (JP)

(72) Inventor: Tomohiko Mamiya, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 649 days.

(21) Appl. No.: 17/062,790

(22) Filed: Oct. 5, 2020

(65) Prior Publication Data

US 2021/0023386 A1 Jan. 28, 2021

Related U.S. Application Data

(63) Continuation of application No. PCT/JP2018/032745, filed on Sep. 4, 2018.

(51) Int. Cl.
*A61B 8/12* (2006.01)
*A61B 17/34* (2006.01)
(Continued)

(52) U.S. Cl.
CPC .............. *A61N 5/0603* (2013.01); *A61B 8/12* (2013.01); *A61B 17/3478* (2013.01);
(Continued)

(58) Field of Classification Search
CPC .......... A61N 5/0603; A61N 2005/0609; A61N 2005/0612; A61N 2005/063; A61N 5/062;
(Continued)

(56) References Cited

U.S. PATENT DOCUMENTS 5,514,669 A 5/1996 Selman
6,315,775 B1 11/2001 Thielen et al.
(Continued)

FOREIGN PATENT DOCUMENTS

AU 2013201683 A1 10/2013
AU 2017248500 A1 11/2017
(Continued)

OTHER PUBLICATIONS

"Characterization of Mediastinal Lymph Node Physiology in Vivo by Optical Spectroscopy during Endoscopic Ultrasound-Guided Fine Needle Aspiration" by S.C. Kanick et al. Journal of Thoracic Oncology. vol. 5, No. 7, pp. 981-987. Jul. 2010 (Year: 2010).*
(Continued)

*Primary Examiner* — Jason M Ip
(74) *Attorney, Agent, or Firm* — Scully, Scott, Murphy & Presser, P.C.

(57) ABSTRACT

A phototherapy method includes: introducing an ultrasound endoscope into a digestive tract; visualizing an irradiation target site in a body by the ultrasound endoscope introduced into the digestive tract; puncturing a vicinity of the irradiation target site with a distal-end section of a needle tube that is made to protrude from a distal-end section of the ultrasound endoscope introduced into the digestive tract; exposing an optical fiber from the distal-end section of the needle tube that has punctured the vicinity of the irradiation target site, by making the needle tube retreat with respect to the optical fiber accommodated inside the needle tube; and radiating light emitted from the exposed optical fiber onto the irradiation target site.

20 Claims, 12 Drawing Sheets

(51) Int. Cl.
*A61M 25/01* (2006.01)
*A61N 5/06* (2006.01)
*A61M 25/00* (2006.01)

(52) U.S. Cl.
CPC .............. *A61B 2017/3413* (2013.01); *A61M 2025/0095* (2013.01); *A61M 25/0108* (2013.01); *A61N 2005/0609* (2013.01); *A61N 2005/0612* (2013.01); *A61N 2005/063* (2013.01)

(58) Field of Classification Search
CPC .............. A61B 8/12; A61B 17/3478; A61B 2017/3413; A61B 1/00098; A61M 25/0108; A61M 2025/0095
See application file for complete search history.

(56) References Cited

U.S. PATENT DOCUMENTS

| | | | |
|---|---|---|---|
| 6,326,548 B1 | 12/2001 | Okumura et al. | |
| 8,512,389 B2* | 8/2013 | Ayala | A61M 25/0662 606/108 |
| 8,951,296 B2* | 2/2015 | Melder | A61B 18/18 606/7 |
| 10,842,556 B1* | 11/2020 | Tandri | A61B 18/1492 |
| 2001/0022234 A1 | 9/2001 | Okumura et al. | |
| 2002/0193850 A1 | 12/2002 | Selman | |
| 2005/0131400 A1* | 6/2005 | Hennings | A61B 18/24 606/15 |
| 2008/0249517 A1 | 10/2008 | Svanberg | |
| 2010/0063392 A1* | 3/2010 | Nishina | A61B 8/4488 600/439 |
| 2010/0063401 A1 | 3/2010 | Nishina et al. | |
| 2012/0010558 A1 | 1/2012 | Kobayashi et al. | |
| 2012/0265057 A1 | 10/2012 | Nishina et al. | |
| 2013/0253266 A1 | 9/2013 | Dextradeur et al. | |
| 2013/0336995 A1 | 12/2013 | Kobayashi et al. | |
| 2014/0120119 A1 | 5/2014 | Kobayashi et al. | |
| 2014/0163371 A1* | 6/2014 | Matsui | A61B 8/12 600/439 |
| 2015/0031956 A1 | 1/2015 | Dextradeur et al. | |
| 2015/0297092 A1 | 10/2015 | Irisawa | |
| 2016/0015829 A1 | 1/2016 | Kobayashi et al. | |
| 2017/0079628 A1 | 3/2017 | Mamiya | |
| 2020/0049874 A1 | 2/2020 | Eckardt | |
| 2020/0085950 A1 | 3/2020 | Kobayashi et al. | |
| 2020/0095331 A1 | 3/2020 | Kobayashi et al. | |

FOREIGN PATENT DOCUMENTS

| | | |
|---|---|---|
| CA | 2809948 A1 | 9/2013 |
| EP | 2449994 A1 | 5/2012 |
| EP | 2641528 A1 | 9/2013 |
| EP | 2944264 A1 | 11/2015 |
| EP | 3266382 A1 | 1/2018 |
| EP | 3329856 A1 | 6/2018 |
| JP | H09-502904 A | 3/1997 |
| JP | 2008-539942 A | 11/2008 |
| JP | 2013-192955 A | 9/2013 |
| JP | 2014-523907 A | 9/2014 |
| JP | 5985131 B1 | 9/2016 |
| JP | 2017-080440 A | 5/2017 |
| WO | WO 95/08949 A1 | 4/1995 |
| WO | WO 2006/121407 A1 | 11/2006 |
| WO | WO 2010/029906 A1 | 3/2010 |
| WO | WO 2013/009475 A1 | 1/2013 |
| WO | WO 2020/049629 A1 | 3/2020 |

OTHER PUBLICATIONS

International Search Report dated Dec. 11, 2018 issued in PCT/JP2018/032745.
"The future of cancer treatment aimed at by photoimmunotherapy", Cancer Plus, Qlife, Inc., Retrieved from the Internet, URL:https://cancer.qlife.jp/immuno/immuno_feature/article10706.html.
"Cylindrical Diffuser, Medlight", Opto Science, Inc., Retrieved from the Internet in Apr. 2018, URL:https://www.pptoscience.com/maker/medlight/lineup/cylindrical_diffuser.html.
"Near-infrared rays kill cancer cells in one day and cure metastatic cancer", Innovation-inspired digital media mugendai, Retrieved from the Internet, URL:https://www.mugendai-web.jp/archives/6080.

* cited by examiner

PHOTOTHERAPY METHOD

CROSS-REFERENCE TO RELATED APPLICATIONS

This is a continuation of International Application PCT/JP2018/032745, with an international filing date of Sep. 4, 2018, which is hereby incorporated by reference herein in its entirety.

TECHNICAL FIELD

The present invention relates to a light-irradiation-device delivery apparatus and a phototherapy method.

BACKGROUND ART

There is a known technique in which, after injection of a drug that accumulates specifically in a cancer cell and that reacts to infrared rays to induce death of the cancer cell, infrared rays are radiated onto the cancer cell by means of an optical fiber inserted into the body (for example, see PTL 1).

CITATION LIST

Patent Literature

{PTL 1} Japanese Translation of PCT International Application, Publication No. 2014-523907

SUMMARY OF INVENTION

One aspect of the present invention is directed to a phototherapy method comprising: introducing an ultrasound endoscope into a digestive tract; visualizing an irradiation target site in a body by means of the ultrasound endoscope introduced into the digestive tract; puncturing a vicinity of the irradiation target site with a distal-end section of a needle tube that is made to protrude from a distal-end section of the ultrasound endoscope introduced into the digestive tract; exposing an optical fiber from the distal-end section of the needle tube that has punctured the vicinity of the irradiation target site, by making the needle tube retreat with respect to the optical fiber accommodated inside the needle tube; and radiating light emitted from the exposed optical fiber onto the irradiation target site.

DESCRIPTION OF EMBODIMENTS

A light-irradiation-device delivery apparatus 1 and a phototherapy method according to one embodiment of the present invention will be described below with reference to the drawings.

Figure 1:
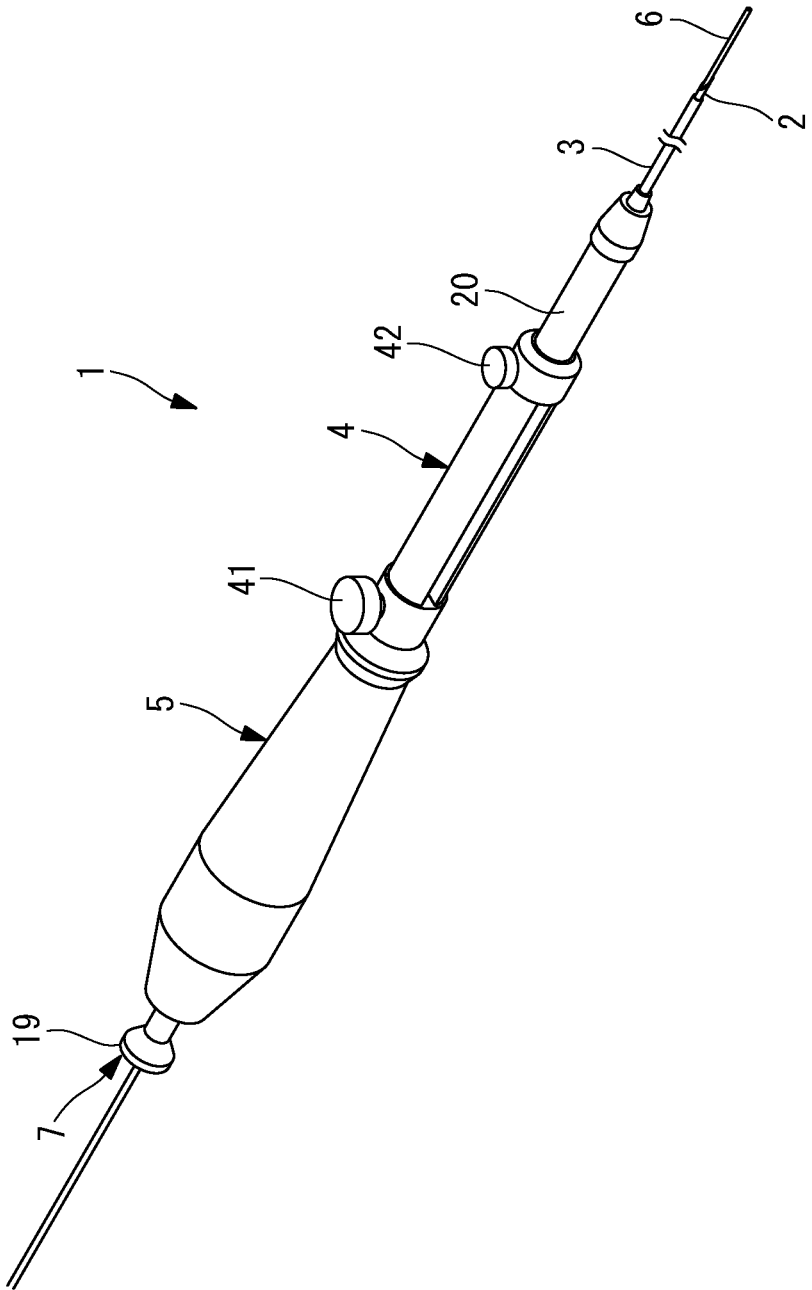
FIG. 1 is a view showing the overall configuration of a light-irradiation-device delivery apparatus according to one embodiment of the present invention.

As shown in FIG. 1, the light-irradiation-device delivery apparatus 1 of this embodiment includes: a metal needle tube 2 that has a longitudinal axis; a flexible sheath 3 that accommodates the needle tube 2 so as to be movable in the longitudinal-axis direction; an attachment adaptor 20 that can be attached to a channel in an ultrasound endoscope 100; a main body 4 to which a proximal end of the sheath 3 is fixed and that is supported so as to be movable in the direction along the longitudinal axis with respect to the attachment adaptor 20; a needle slider 5 that is supported so as to be movable in the direction along the longitudinal axis with respect to the main body 4; and an optical fiber 6 that is accommodated inside the needle tube 2 so as to be movable in the longitudinal-axis direction. Furthermore, it is preferred that the light-irradiation-device delivery apparatus 1 of this embodiment include a fixing mechanism 7 that detachably fixes the optical fiber 6, at an intermediate position thereof in the longitudinal direction, to a proximal-end section of the needle slider 5.

A proximal end of the needle tube 2 is fixed to a proximal end of the needle slider 5. The fixing mechanism 7 is attached to the proximal end of the needle slider 5. The main body 4 is provided with: a stopper 41 that adjustably defines a forward position of the needle slider 5 with respect to the main body 4; and a fixing screw 42 that fixes the main body 4 at an arbitrary position with respect to the attachment adaptor 20.

Figure 2:
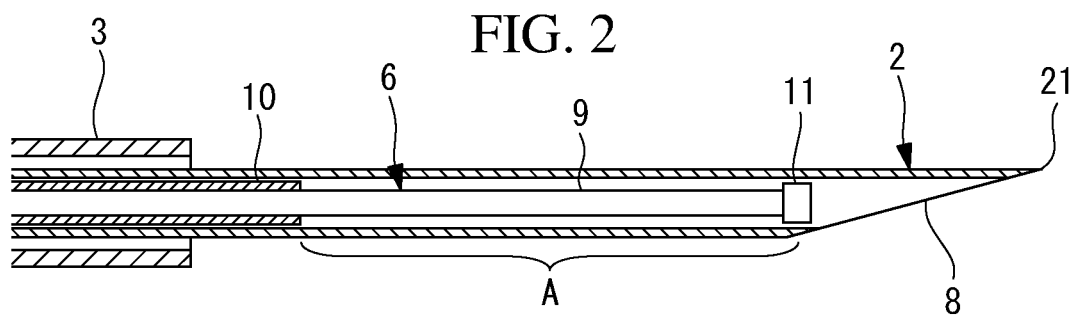
FIG. 2 is a longitudinal sectional view showing a needle tube provided in the light-irradiation-device delivery apparatus shown in FIG. 1.

As shown in FIG. 2, the needle tube 2 is formed in a cylindrical shape and has: a blade surface 8 that has a shape obtained by diagonally cutting a distal end thereof in a plane intersecting the longitudinal axis.

The proximal end of the needle tube 2 is fixed to the proximal end of the needle slider 5, and the needle tube 2 is made to advance and retreat in the longitudinal-axis direction with respect to the sheath 3 through movement of the needle slider 5 in the longitudinal-axis direction with respect to the main body 4.

The proximal end of the sheath 3 is fixed to the main body 4, and the sheath 3, which is fixed to the main body 4, is made to advance and retreat in the longitudinal-axis direction integrally with the needle tube 2, which is fixed to the needle slider 5, through movement of the main body 4 in the longitudinal-axis direction with respect to the attachment adaptor 20.

As shown in FIG. 2, the optical fiber 6 includes a core 9 through which light propagates and a clad 10 that covers an outer circumferential surface of the core 9, and also includes, at a distal-end section of the optical fiber 6, an emission area A where the core 9 is exposed by partially peeling off the clad 10. A light source (not shown) that emits near infrared light (light) is connected to a proximal end of the optical fiber 6.

A marker 11 that is made of metal, for example, tantalum, is disposed at a distal-end position of the emission area A. The marker 11 is formed in a ring shape, is disposed at such a position as to cover the entire outer circumference of the core 9 of the optical fiber 6, and is fixed to the core 9 by an arbitrary method, such as press fitting or bonding.

Figure 3:
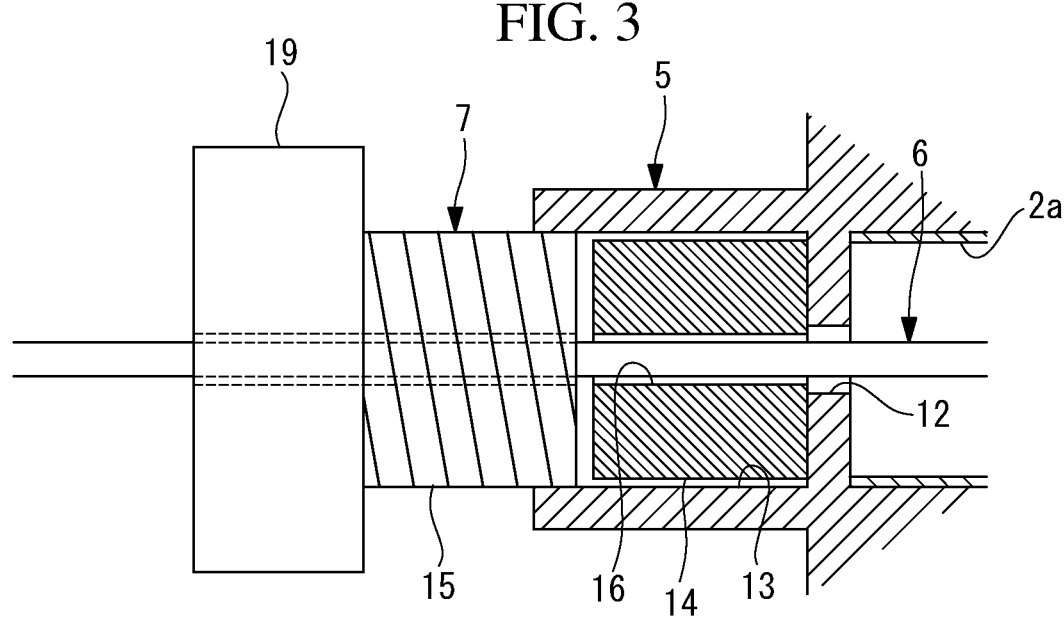
FIG. 3 is a longitudinal sectional view showing an example fixing mechanism provided in the light-irradiation-device delivery apparatus shown in FIG. 1.
Figure 4:
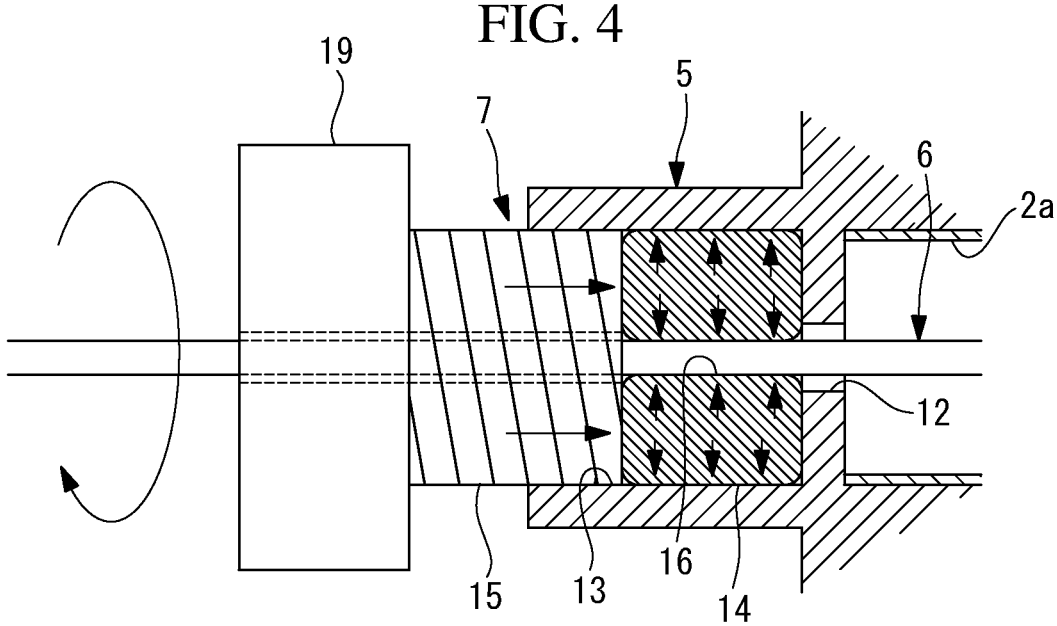
FIG. 4 is a longitudinal sectional view showing a state in which an optical fiber is fixed to a needle slider by the fixing mechanism shown in FIG. 3.

The fixing mechanism 7 detachably fixes the optical fiber 6 to the needle slider 5 in a state in which the optical fiber 6 is inserted into the needle tube 2 from the proximal end of the needle tube 2, and, as shown in FIGS. 3 and 4, for example, includes: a screw hole 13 that is provided so as to have a predetermined depth from the proximal end of the needle slider 5 to a proximal end of an insertion hole 12 connected to an inner hole 2a of the needle tube 2 and so as to be coaxial with the insertion hole 12 and have a larger diameter than the insertion hole 12; a cylindrical elastic body 14 through which the optical fiber 6 is inserted and that is accommodated in the screw hole 13; a compression member 15 that is fastened into the screw hole 13, thereby compressing the elastic body 14 in the axial direction; and a grip portion 19 that is attached to a proximal end of the compression member 15.

When an operator rotates the grip portion 19 to fasten the compression member 15 into the screw hole 13, the elastic body 14 sandwiched between the bottom of the screw hole 13 and the compression member 15 is compressed in the axial direction, thus reducing the inner diameter of a through hole 16 of the cylindrical elastic body 14. Accordingly, as shown in FIG. 4, the optical fiber 6, which is inserted through the through hole 16, is tightened radially inward by the elastic body 14, thus making it possible to easily fix the optical fiber 6 to the needle slider 5. Urethane rubber, for example, can be used as the elastic body 14.

The phototherapy method using the light-irradiation-device delivery apparatus 1 of this embodiment will be described below.

A description will be given below of an example case in which the phototherapy method of this embodiment is applied to a cancer cell present in the pancreas.

Figure 5:
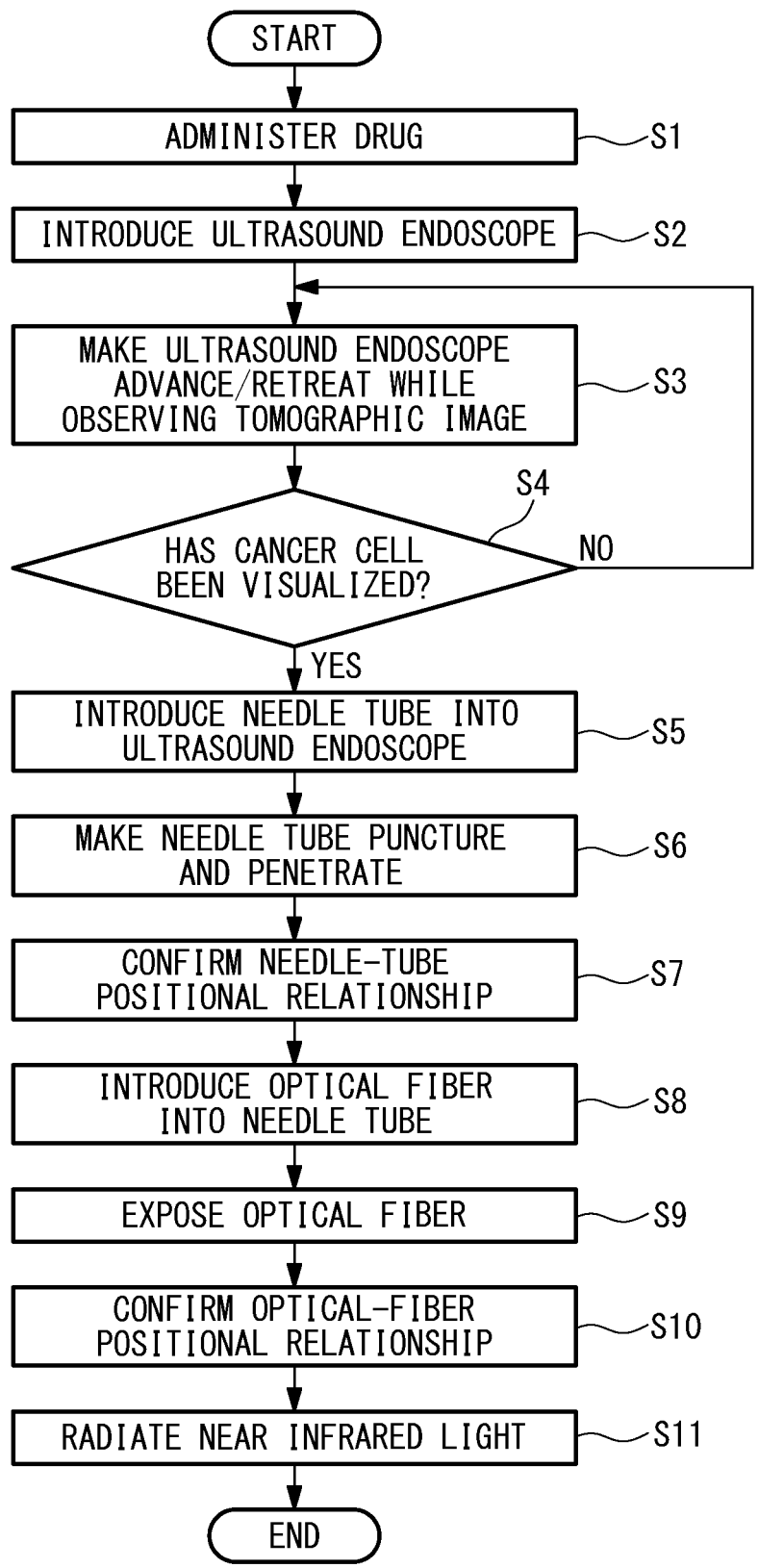
FIG. 5 is a flowchart for explaining a phototherapy method according to the embodiment of the present invention.

As shown in FIG. 5, in the phototherapy method of this embodiment, a drug that reacts to near infrared light to damage a cancer cell (irradiation target site) X through heat generation etc., thereby inducing cell death of the cancer cell, is administered to a patient in advance (Step S1), and the ultrasound endoscope 100 is introduced into the digestive tract Y, such as the stomach or the duodenum (Step S2).

The ultrasound endoscope 100 is made to advance or retreat while observing the cancer cell X present in a tomographic image of an organ, for example, the pancreas, adjacent to the digestive tract Y by means of the ultrasound endoscope 100 (Step S3), and the ultrasound endoscope 100 is disposed at a position where the cancer cell X can be visualized (Step S4).

Figure 6:
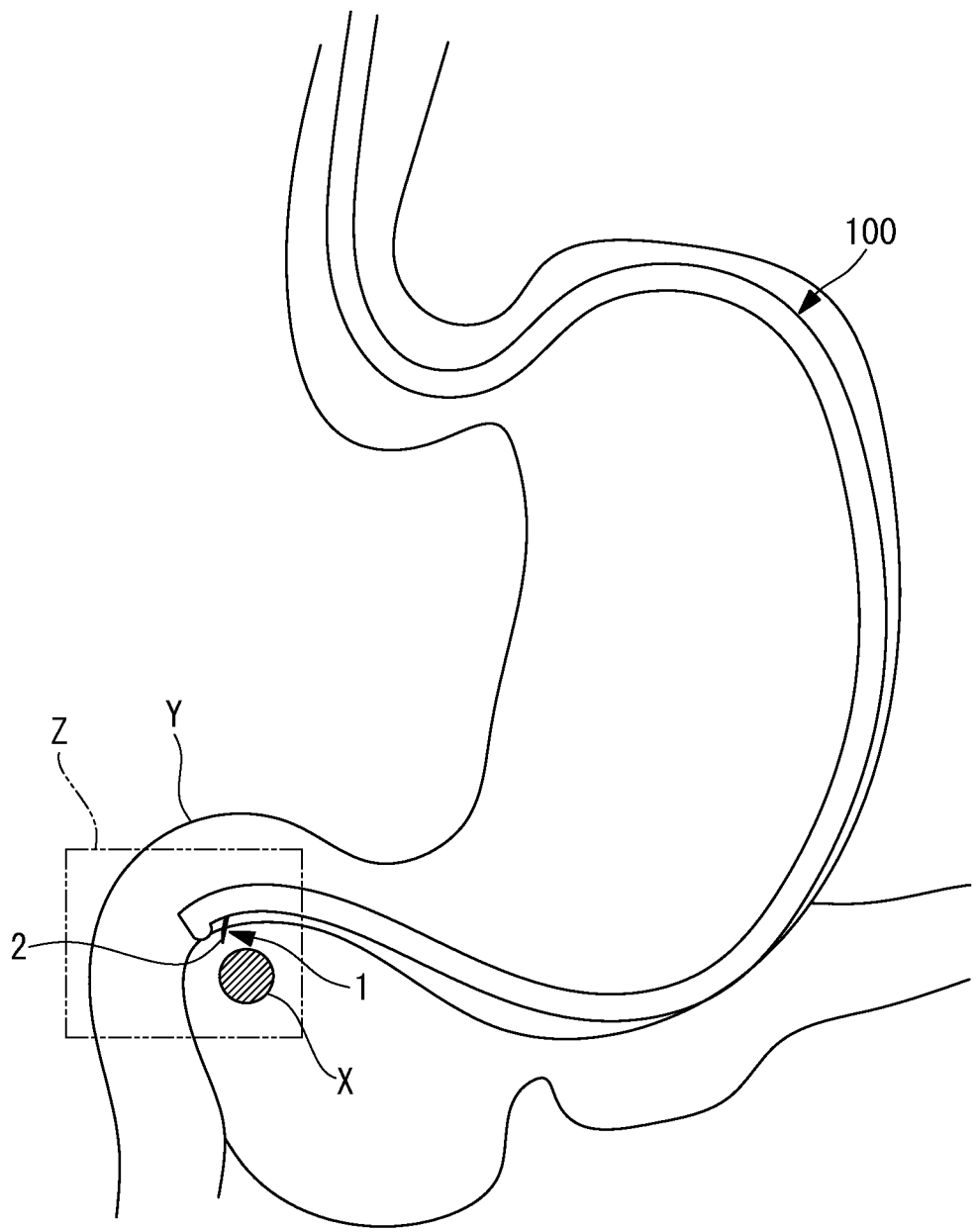
FIG. 6 is a view showing a state in which the needle tube, which has penetrated a digestive tract, is disposed in the vicinity of a cancer cell present outside the digestive tract, in the phototherapy method shown in FIG. 5.

When the ultrasound endoscope 100 is inserted up to the position where the cancer cell X can be visualized, the light-irradiation-device delivery apparatus 1 is made to protrude, via the channel provided in the ultrasound endoscope 100, from a distal end of the channel in the ultrasound endoscope 100 (Step S5). At this time, the attachment adaptor 20 is attached to the channel in the ultrasound endoscope 100. Then, as shown in FIG. 6, the needle tube 2 is made to protrude from a distal-end opening of the channel in the ultrasound endoscope 100, the needle tube 2 punctures the wall of the digestive tract Y, and the needle tube 2 is made to penetrate the wall of the digestive tract Y and punctures the pancreas adjacent to the digestive tract Y (Step S6). Specifically, the needle tube 2 punctures an inner wall of the stomach or the duodenum and punctures the pancreas after the needle tube 2 penetrates the inner wall of the stomach or the duodenum. Accordingly, the needle tube 2 punctures the vicinity of the cancer cell X present in the pancreas.

Figure 7:
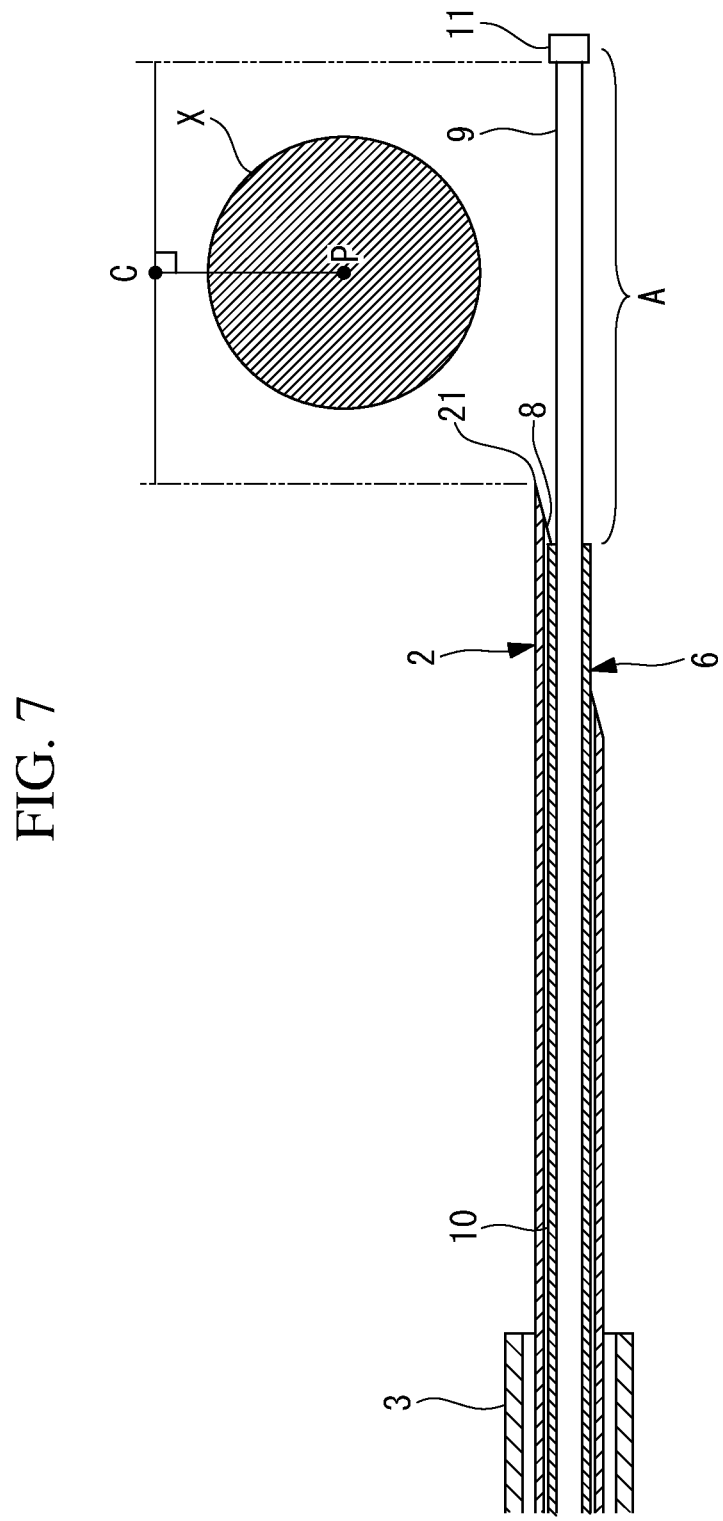
FIG. 7 is a view showing a state in which the optical fiber is exposed from a blade surface of the needle tube shown in FIG. 6.

Because the needle tube 2 is made of metal, it is possible to reliably visually confirm the needle tube 2 in an ultrasound image acquired by the ultrasound endoscope 100. The operator confirms the positional relationship between the needle tube 2 and the cancer cell X, in the ultrasound image (Step S7), and stops the needle tube 2 when a distal end of the needle tube 2 is disposed in the vicinity of the cancer cell X, as shown in FIG. 6. Then, the optical fiber 6 is introduced into the needle tube 2 of the light-irradiation-device delivery apparatus 1 (Step S8), and the optical fiber 6 is exposed at a side closer to the distal end than the blade surface 8 is, as shown in FIG. 7 (Step S9).

Figure 8:
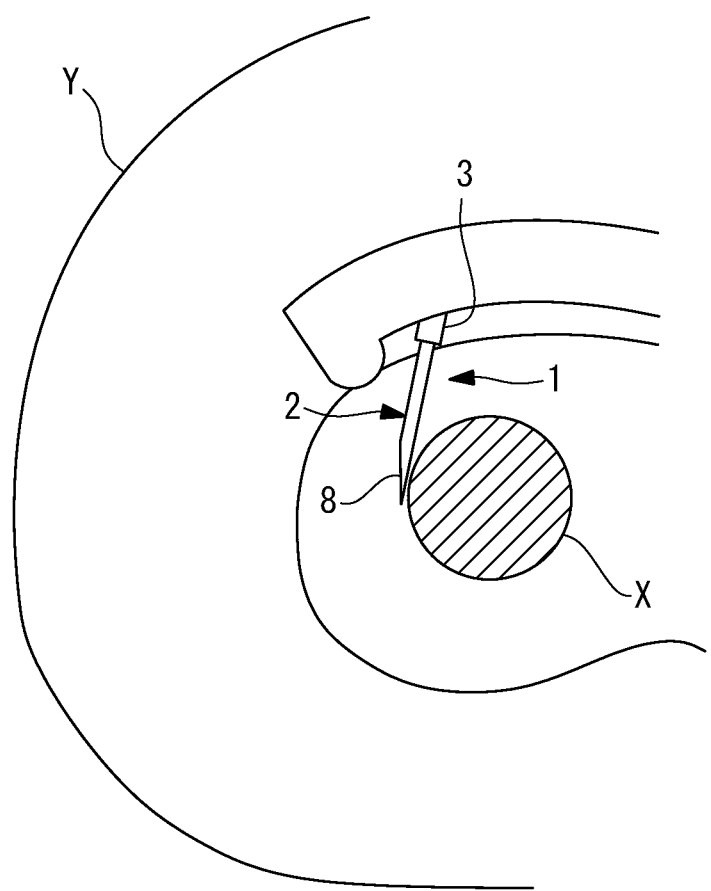
FIG. 8 is an enlarged view of a Z-portion shown in FIG. 6.
Figure 9:
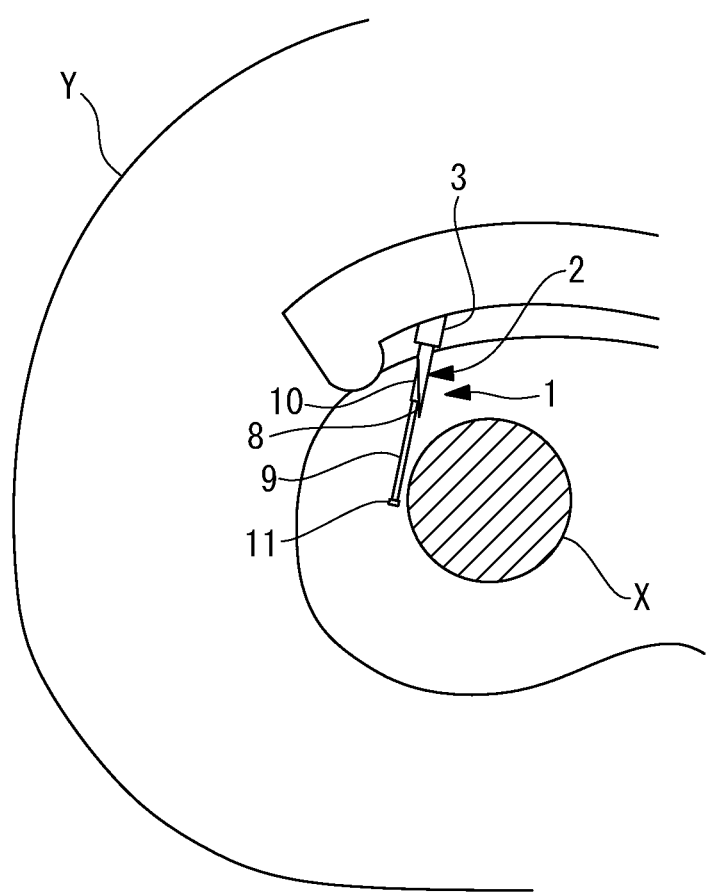
FIG. 9 is an enlarged view showing a state in which the optical fiber is exposed from the state shown in FIG. 8.

Specifically, as shown in FIG. 8, the needle tube 2 is made to retreat with respect to the optical fiber 6 in a state in which the distal end of the needle tube 2 inserted through the digestive tract Y is disposed in the vicinity of the cancer cell X, thereby exposing the optical fiber 6 at a side closer to the distal end than the blade surface 8 is, as shown in FIG. 9. Accordingly, compared with a case in which the optical fiber 6 is made to protrude from the blade surface 8 by pressing the optical fiber 6 with respect to the needle tube 2, it is possible to suppress the load acting on the optical fiber 6.

Because the metal marker 11 is disposed at a distal end of the optical fiber 6, it is possible to reliably visually confirm the position of the marker 11 in an ultrasound image acquired by the ultrasound endoscope 100. The operator confirms the positional relationship among the distal end of the needle tube 2, the marker 11, and the cancer cell X, in the ultrasound image (Step S10). As shown in FIG. 7, when the marker 11 is disposed at such a position that the line segment connecting a needle point 21 of the needle tube 2 and the marker 11 is opposed to the cancer cell X, i.e., at such a position that a perpendicular line from a middle point C of the line segment passes through substantially the center P of the cancer cell X, near infrared light from the light source is made to enter the optical fiber 6. Note that, after Step S10, the operator may operate the grip portion 19 of the fixing mechanism 7 to position the distal end of the optical fiber 6.

The near infrared light that has been made to enter the optical fiber 6 propagates in the core 9 of the optical fiber 6 up to the distal end and is emitted in all radial directions from the emission area A, which is provided at the distal end. Because the emission area A is positioned at the position opposed to the cancer cell X, the near infrared light emitted from the emission area A is radiated onto the cancer cell X located at a radially outer side (Step S11). Accordingly, the drug that has been administered in advance reacts to the near infrared light to generate heat, thus making it possible to induce death of the cancer cell X.

Specifically, according to the light-irradiation-device delivery apparatus 1 and the phototherapy method of this embodiment, there is an advantage in that it is possible to precisely align the emission area A of the optical fiber 6 with the cancer cell X, with the marker 11 and the needle point 21 of the needle tube 2 serving as marks, and to reliably and efficiently radiate the near infrared light onto the cancer cell X from the precisely aligned emission area A of the optical fiber 6.

Specifically, it is difficult to visually confirm the core 9 of the optical fiber 6, which is made of resin or glass, in an ultrasound image. According to this embodiment, however, the metal needle tube 2 and the metal marker 11 can be visually confirmed well in an ultrasound image. Therefore, the emission area A can be more reliably aligned with the cancer cell X by confirming the positional relationship among the needle tube 2, the marker 11, and the cancer cell X.

Figure 10:
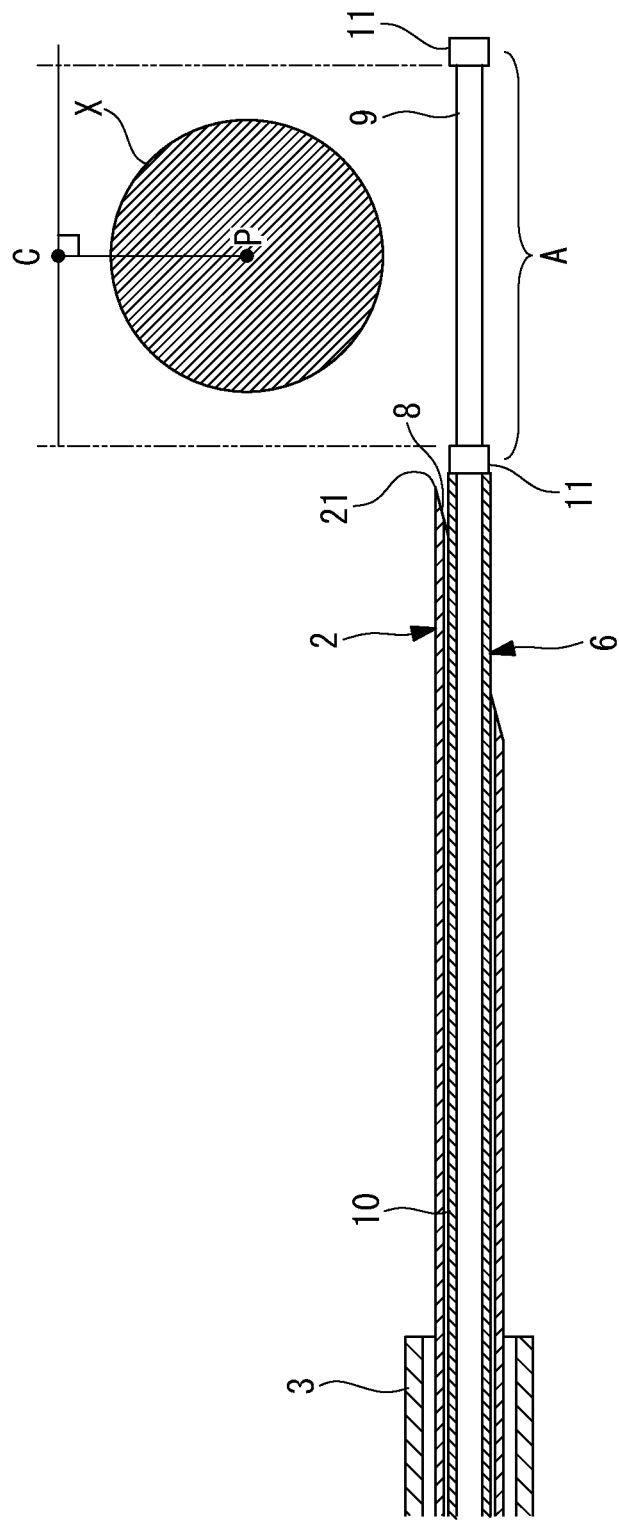
FIG. 10 is a longitudinal sectional view showing a modification of a marker attachment position in the light-irradiation-device delivery apparatus shown in FIG. 1.

Note that, in this embodiment, although the metal marker 11 is provided only at a distal end of the emission area A of the optical fiber 6, in addition to this, as shown in FIG. 10, the metal marker 11 may be provided also at a proximal end of the emission area A. In the case in which the metal marker 11 is provided only at the distal end of the emission area A, the proximal end of the emission area A can be recognized with the needle point 21 of the needle tube 2; however, in a case in which the proximal end of the emission area A is made to protrude farther beyond the needle point 21, when the marker 11 is provided also at the proximal end of the emission area A, it is possible to easily visually confirm the position of the emission area A, irrespective of the position of the emission area A with respect to the needle point 21. In particular, this structure is also effective in a case in which a needle tube 2 that is made of a material other than metal is used.

Figure 11:
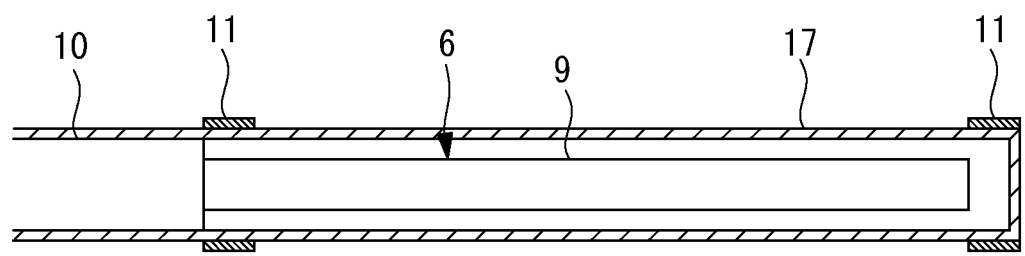
FIG. 11 is a longitudinal sectional view showing a first modification of the optical fiber accommodated inside the needle tube, in the light-irradiation-device delivery apparatus shown in FIG. 1.
Figure 12:
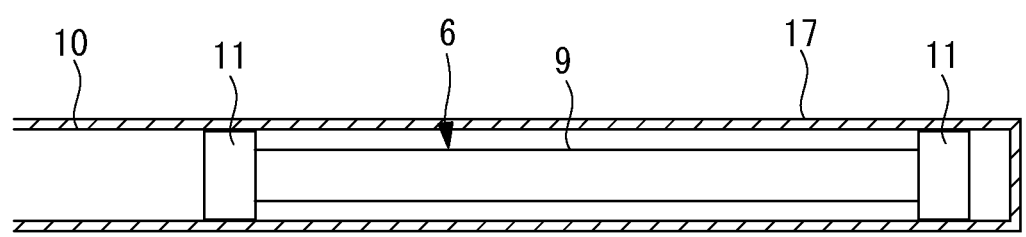
FIG. 12 is a longitudinal sectional view showing a second modification of the optical fiber accommodated inside the needle tube, in the light-irradiation-device delivery apparatus shown in FIG. 1.
Figure 13:
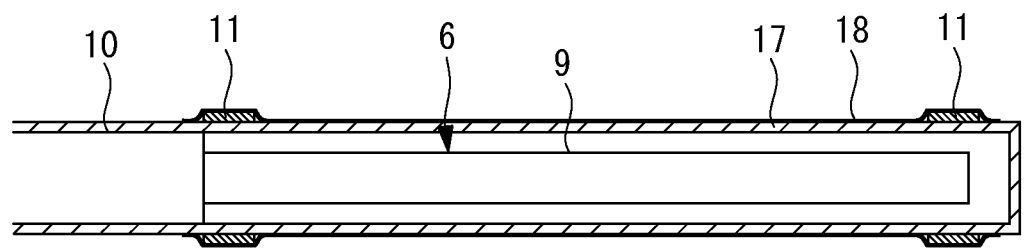
FIG. 13 is a longitudinal sectional view showing a third modification of the optical fiber accommodated inside the needle tube, in the light-irradiation-device delivery apparatus shown in FIG. 1.

Furthermore, in this embodiment, although a description has been given of a case in which the optical fiber 6 is directly accommodated inside the needle tube 2, instead of this, as shown in FIG. 11, the optical fiber 6 may be accommodated inside a white, transparent, or translucent protective tube 17. In this case, the markers 11 may be fixed to an outer surface of the protective tube 17 through caulking or bonding, as shown in FIG. 11, or may be accommodated inside the protective tube 17 in a state in which the markers 11 are fixed inside the protective tube 17 through press fitting or bonding, as shown in FIG. 12. Furthermore, as shown in FIG. 13, when the markers 11 are fixed to the outer surface of the protective tube 17, a heat-shrinkable tube 18 that is made of a transparent or translucent material may be made to shrink from the outside, thus preventing the markers 11 from falling off.

Furthermore, in this embodiment, although the marker 11 is formed in a ring shape and is disposed all around the circumference of the core 9, instead of this, the marker 11 may be disposed at a circumferential section of the core 9. Furthermore, the marker 11 to be fixed at the distal end of the optical fiber 6 may be fixed to a distal-end surface of the core 9.

Furthermore, in this embodiment, although the cancer cell X, such as pancreatic cancer, is illustrated as the irradiation target site, and near infrared light is illustrated as light radiated onto the cancer cell X, instead of this, it is also possible to radiate another arbitrary type of light having a therapeutic effect onto another arbitrary irradiation target site X.

Figure 14:
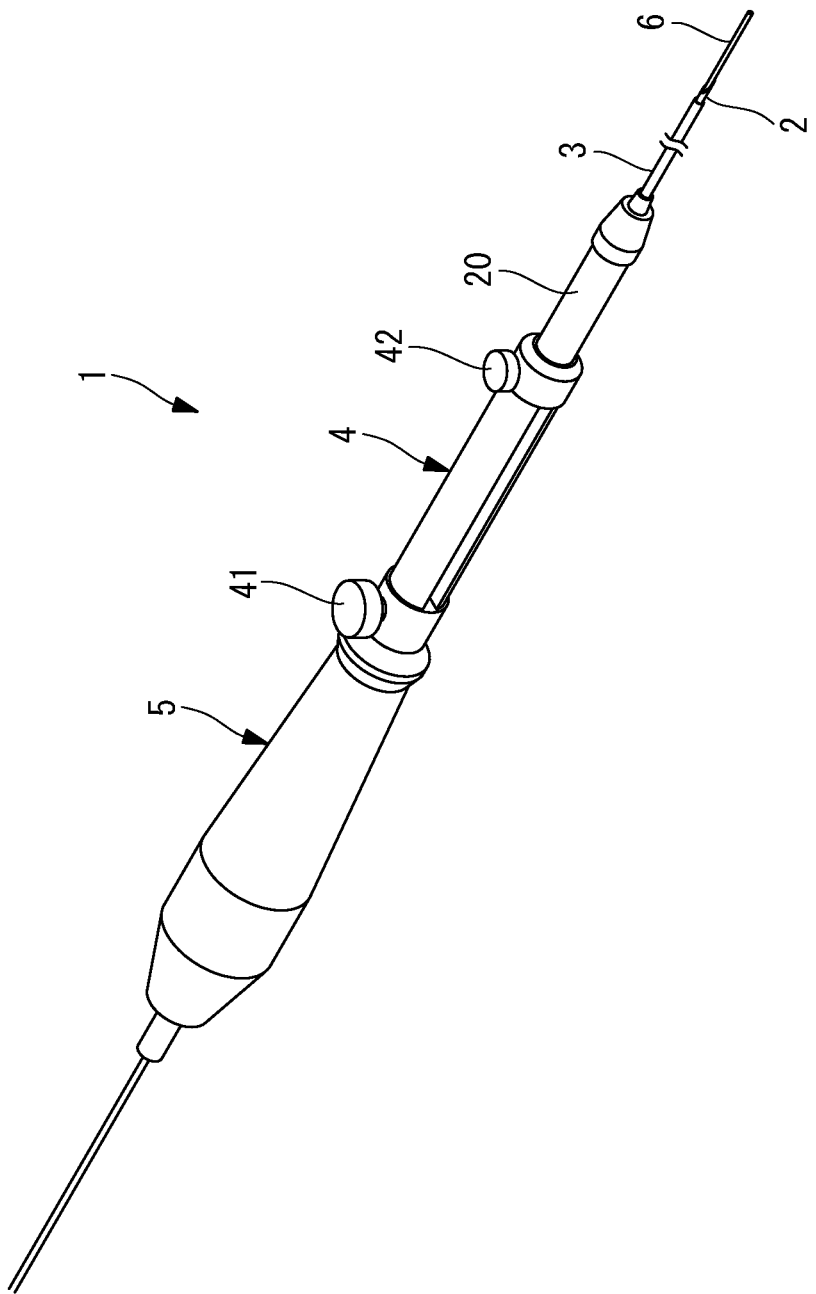
FIG. 14 is a view showing the overall configuration of a modification of the light-irradiation-device delivery apparatus shown in FIG. 1.

Furthermore, in the light-irradiation-device delivery apparatus 1 of this embodiment, although the fixing mechanism 7 is included, instead of this, as shown in FIG. 14, the fixing mechanism 7 need not be included.

Furthermore, in the light-irradiation-device delivery apparatus 1 of this embodiment, although the optical fiber 6 is used, instead of this, an LED, organic electroluminescent device, or the like may be used.

Figure 15:
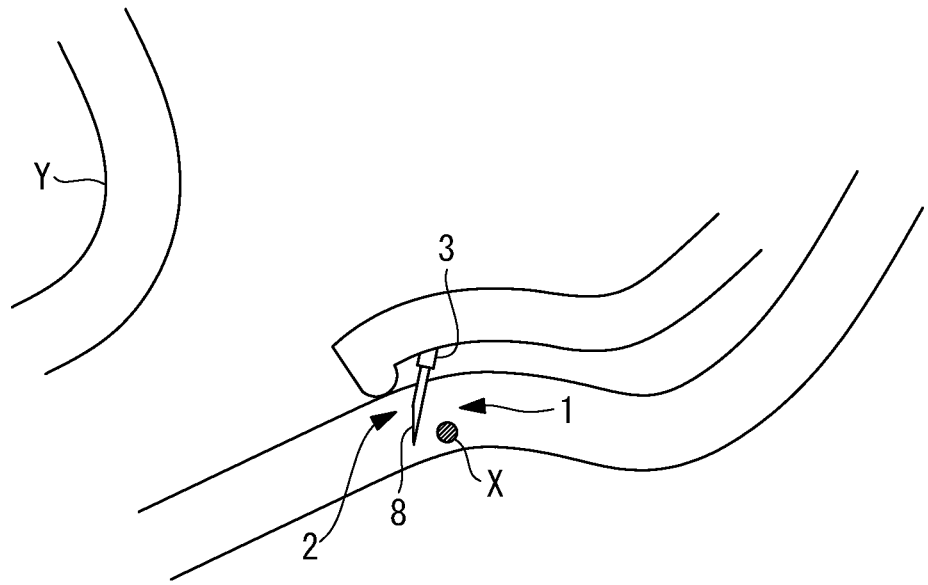
FIG. 15 is a view showing a state in which the needle tube that has punctured the wall of the digestive tract is disposed in the vicinity of a cancer cell present inside the wall of the digestive tract, in a modification of the phototherapy method shown in FIG. 5.
Figure 16:
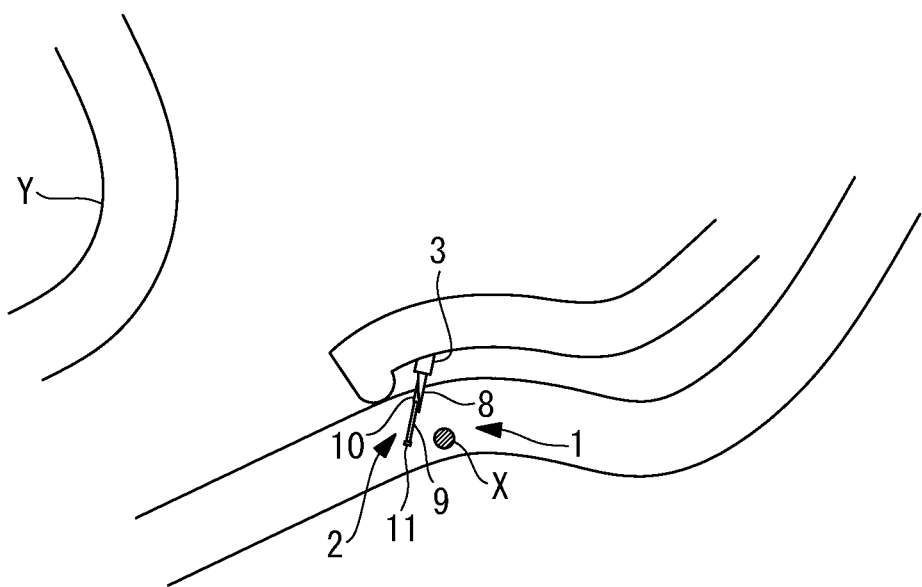
FIG. 16 is a view showing a state in which the optical fiber is exposed from the blade surface of the needle tube shown in FIG. 15.

Furthermore, in this embodiment, although an example case in which the cancer cell X is present in an organ adjacent to the digestive tract Y is illustrated, instead of this, the present invention may be applied to a case in which the cancer cell X is present in another place, for example, in the wall of the digestive tract Y, as shown in FIGS. 15 and 16. FIGS. 15 and 16 show an example case in which the cancer cell X is present in the wall of the stomach. In this case, the cancer cell X present in a tomographic image of the wall of the digestive tract Y is confirmed in Step S3, and the needle tube 2 punctures a mucosal surface of the digestive tract Y toward an outer side of the digestive tract Y up to a position in the vicinity of the cancer cell X in the wall of the digestive tract Y, in Step S6. In the other Steps S1, S2, S4, S5, S7, S8, S9, S10, and S11, the same processing is basically carried out.

Figure 17:
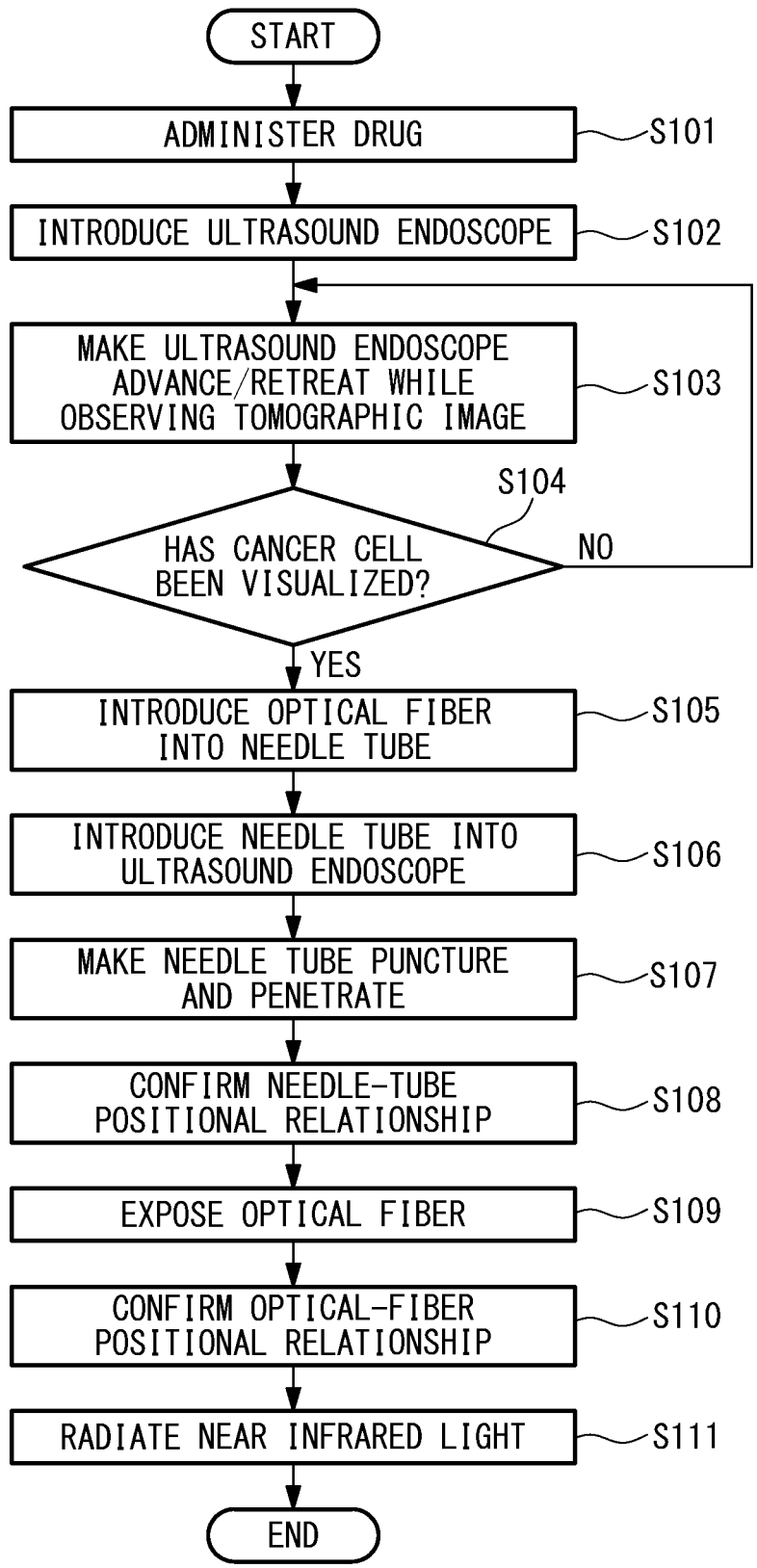
FIG. 17 is a flowchart for explaining the modification of the phototherapy method shown in FIG. 5.

Furthermore, in the phototherapy method using the light-irradiation-device delivery apparatus 1 of this embodiment, although, the optical fiber 6 is introduced into the needle tube 2 (Step S8) after the needle tube 2 is stopped, instead of this, as shown in FIG. 17, it is also possible to adopt a method in which, after the ultrasound endoscope 100 is moved to a position where the cancer cell X is visualized (Step S104), the optical fiber 6 is introduced into the needle tube 2 (Step S105), and the needle tube 2 of the light-irradiation-device delivery apparatus 1 is introduced into the ultrasound endoscope 100 (Step S106).

Specifically, a drug that reacts to the near infrared light L to damage the cancer cell (irradiation target site) X through heat generation etc., thereby inducing cell death of the cancer cell, is administered to a patient in advance (Step S101), and the ultrasound endoscope 100 is introduced into the digestive tract Y such as the stomach or the duodenum (Step S102).

The ultrasound endoscope 100 is made to advance or retreat while observing the cancer cell X present in a tomographic image of the pancreas adjacent to the digestive tract Y by means of the ultrasound endoscope 100 (Step S103), and the ultrasound endoscope 100 is disposed at a position where the cancer cell X can be visualized (Step S104).

When the ultrasound endoscope 100 is inserted up to the position where the cancer cell X can be visualized, the optical fiber 6 is introduced into the needle tube 2 of the light-irradiation-device delivery apparatus 1 (Step S105).

Then, the light-irradiation-device delivery apparatus 1 of this embodiment is made to protrude, via the channel provided in the ultrasound endoscope 100, from the distal end of the channel in the ultrasound endoscope 100 (Step S106). At this time, the attachment adaptor 20 is attached to the channel in the ultrasound endoscope 100. Then, the needle tube 2 is made to protrude from the distal-end opening of the channel in the ultrasound endoscope 100, the needle tube 2 punctures the wall of the digestive tract Y, and the needle tube 2 is made to penetrate the wall of the digestive tract Y and punctures the pancreas adjacent to the digestive tract Y (Step S107).

The operator confirms the positional relationship between the needle tube 2 and the cancer cell X, in an ultrasound image (Step S108). The needle tube 2 is stopped when the distal end of the needle tube 2 is disposed in the vicinity of the cancer cell X. Then, the optical fiber 6 is exposed at a side closer to the distal end than the blade surface 8 is (Step S109).

Because the metal marker 11 is disposed at the distal end of the optical fiber 6, the position of the marker 11 can be reliably visually confirmed in an ultrasound image acquired by the ultrasound endoscope 100. The operator confirms the positional relationship among the distal end of the needle tube 2, the marker 11, and the cancer cell X, in the ultrasound image (Step S10). As shown in FIG. 7, when the marker 11 is disposed at such a position that the line segment connecting the needle point 21 of the needle tube 2 and the marker 11 is opposed to the cancer cell X, i.e., at such a position that a perpendicular line from the middle point C of the line segment passes through substantially the center P of the cancer cell X, near infrared light from the light source is made to enter the optical fiber 6.

The near infrared light L that has been made to enter the optical fiber 6 propagates in the core 9 of the optical fiber 6 up to the distal end and is emitted in all radial directions from the emission area A, which is provided at the distal end. Because the emission area A is positioned at the position opposed to the cancer cell X, the near infrared light emitted from the emission area A is radiated onto the cancer cell X located at a radially outer side (Step S111).

Note that it is preferred that, after the optical fiber 6 is introduced into the needle tube 2 (Step S10) and before the needle tube 2 is inserted into the channel in the ultrasound endoscope 100 (Step S6), the optical fiber 6 that has been inserted into the needle tube 2 be fixed by the compression member 15 of the fixing mechanism 7. In this case, after the needle tube 2 is stopped (Step S9) and before the optical fiber 6 is exposed from the distal end of the needle tube 2 (Step S11), the operator rotates the grip portion 19 to loosen the fastening of the compression member 15 of the fixing mechanism 7 into the screw hole 13, thereby restoring the elastically deformed elastic body 14 and releasing the fixed state of the optical fiber 6 with respect to the main body 4. Accordingly, it is possible to prevent misalignment of the optical fiber 6 with respect to the needle tube 2.

As a result, the above-described embodiment leads to the following aspects.

One aspect of the present invention is directed to a light-irradiation-device delivery apparatus including: a needle tube that has a longitudinal axis and that has a blade surface at a distal end; and an optical fiber that is disposed inside the needle tube so as to be movable in the longitudinal axis, wherein the optical fiber includes a core through which light propagates and a clad that covers an outer circumferential surface of the core and also includes, at a distal-end section thereof that can be exposed from the blade surface of the needle tube, an emission area from which the light that has propagated is emitted radially outward; the emission area is configured by peeling off the clad and exposing the core; and a metal marker is disposed at a distal-end position of the emission area.

According to this aspect, the tubular needle tube is introduced into the body of a patient via a channel in an ultrasound endoscope inserted into a digestive tract, and the blade surface of the needle tube is made to protrude from a distal-end opening of the channel, thereby making the blade surface penetrate the wall of the digestive tract. The emission area, which is located at the distal end of the optical fiber, is exposed from the blade surface disposed in the vicinity of an irradiation target site, for example, a pancreatic tumor, that is present outside the digestive tract, and light supplied from a proximal end of the optical fiber is emitted from the emission area, with the core being exposed by peeling off the clad, thereby making it possible to radiate the emitted light onto the irradiation target site.

In this case, although the core of the optical fiber is made of a material, such as glass or resin, that hardly reflects ultrasound, the marker, which is disposed at the distal end of the emission area, is made of metal, thereby making it possible to clearly visually confirm the marker in an ultrasound image acquired by the ultrasound endoscope. Therefore, the positional relationship between the irradiation target site and the marker is confirmed in the ultrasound image, thereby making it possible to appropriately align the emission area of the optical fiber with the irradiation target site and to efficiently radiate light emitted from the emission area onto the irradiation target site.

In the above-described aspect, a metal marker may be disposed at a proximal end position of the emission area.

With this configuration, because the emission area is disposed in a region sandwiched between the two markers, the positional relationship among the irradiation target site and the two markers is confirmed in an ultrasound image, thereby making it possible to more appropriately align the emission area with the irradiation target site.

Furthermore, in the above-described aspect, the marker may cover all around the outer circumference of the optical fiber.

With this configuration, even when the optical fiber is disposed at any position about the longitudinal axis, it is possible to reflect, at the marker, ultrasound generated by the ultrasound endoscope and to make an image of the marker in the ultrasound image clear.

Furthermore, in the above-described aspect, the needle tube may be made of metal.

With this configuration, because the emission area is disposed in a region sandwiched between the marker and the needle tube, the positional relationship among the irradiation target site, the needle tube, and the marker is confirmed in the ultrasound image, thereby making it possible to more appropriately align the emission area with the irradiation target site.

Another aspect of the present invention is directed to a phototherapy method including: introducing an ultrasound endoscope into a digestive tract; visualizing an irradiation target site in a body by means of the ultrasound endoscope introduced into the digestive tract; puncturing the vicinity of the irradiation target site with a distal-end section of a needle tube that is made to protrude from a distal-end section of the ultrasound endoscope introduced into the digestive tract; exposing an optical fiber from the distal-end section of the needle tube that has punctured the vicinity of the irradiation target site, by making the needle tube retreat with respect to the optical fiber accommodated inside the needle tube; and radiating light emitted from the exposed optical fiber onto the irradiation target site.

According to this aspect, a drug that accumulates specifically in an irradiation target site, for example, a cancer cell, is injected in advance, the ultrasound endoscope is inserted into a digestive tract, the needle tube that has accommodated the optical fiber is inserted via a channel in the ultrasound endoscope, and a distal-end section of the needle tube made to protrude from a distal-end opening of the channel punctures the vicinity of the irradiation target site. Then, the needle tube is made to retreat with respect to the optical fiber, which is accommodated inside the needle tube, thereby exposing the optical fiber from the needle tube, and the positional relationship between the marker and the irradiation target site is confirmed in an ultrasound image acquired by the ultrasound endoscope, thereby making it possible to more appropriately align the optical fiber with the irradiation target site. Accordingly, light emitted from the optical fiber is radiated onto the irradiation target site without being wasted, thus making it possible to effectively treat the irradiation target site.

In the above-described aspect, the optical fiber may have an emission area at a distal end, and a metal marker may be disposed at a distal end of the emission area; and the phototherapy method may further include confirming, before light emitted from the optical fiber is radiated onto the irradiation target site, the positional relationship between the marker and the irradiation target site, in an ultrasound image acquired by the ultrasound endoscope.

Furthermore, in the above-described aspect, a metal marker may be disposed at a proximal end position of the emission area.

Furthermore, in the above-described aspect, the marker may cover the entire outer circumference of the optical fiber.

Furthermore, the above-described aspect may further include disposing the ultrasound endoscope at a position in the digestive tract where the irradiation target site can be visualized, while observing the irradiation target site in a tomographic image of an organ adjacent to the digestive tract by means of the ultrasound endoscope.

Furthermore, in the above-described aspect, the digestive tract may be the stomach or the duodenum; the irradiation target site may be a cancer cell present in the pancreas; and the puncturing the vicinity of the irradiation target site may include puncturing, with the needle tube, an inner wall of the stomach or the duodenum through to the inside of the pancreas.

Furthermore, in the above-described aspect, the digestive tract may be the stomach; the irradiation target site may be a cancer cell present in a stomach wall of the stomach; and the puncturing the vicinity of the irradiation target site may include puncturing, with the needle tube, until a needle point of the needle tube is positioned inside the stomach wall.

REFERENCE SIGNS LIST 1 light-irradiation-device delivery apparatus
2 needle tube
6 optical fiber
8 blade surface
9 core
10 clad
11 marker
100 ultrasound endoscope
A emission area
X cancer cell (irradiation target site)
Y digestive tract

The invention claimed is:

1. A phototherapy method comprising:
introducing an endoscope into a digestive tract;
while introducing the endoscope into the digestive tract, protruding a needle tube from a distal-end of the endoscope to puncture a vicinity of an irradiation target site with the needle tube;
subsequent to the protruding, advancing the needle tube to the irradiation target site;
during or after the protruding, advancing an optical fiber into at least a portion of the needle tube that is advanced to the irradiation target site, wherein a first marker is disposed distally relative to the core exposed at the distal portion of the optical fiber;
subsequent to the advancing of the optical fiber, retracting the needle tube to expose light emitted from an outer circumferential surface of a portion of the optical fiber exposed from the needle tube to the irradiation target site;
subsequent to the retracting, and while maintaining a positional relationship between a location on the optical fiber exposed from the needle tube and a distal end of the needle tube, circumferentially radiating the light emitted from the portion of the optical fiber onto the irradiation target site;
acquiring an ultrasound image, the ultrasound image including the irradiation target site; and
determining a positional relationship between the first marker and the irradiation target site, in the acquired ultrasound image;
wherein the optical fiber has a core and a clad covering the core, the portion of the optical fiber comprises a circumferential surface of the core exposed at a distal portion of the optical fiber;
the clad is provided proximally relative to the exposed circumferential surface of the core;
a protective tube, other than the needle tube, is provided to cover the core exposed at the distal portion of the optical fiber; and
the advancing of the optical fiber comprises advancing at least the distal portion of the optical fiber having the exposed core and a corresponding portion of the protective tube into at least the portion of the needle tube.

2. The phototherapy method according to claim 1, wherein the determining determines that the irradiation target site is disposed in a direction perpendicular to one of a longitudinal direction of the needle tube and a line segment connecting the distal end of the needle tube and the first marker, in the acquired ultrasound image; and
the location is the first marker provided distally relative to the core exposed at the distal portion of the optical fiber.

3. The phototherapy method according to claim 1, wherein one of the optical fiber, the protective tube or the needle tube comprising a second marker disposed proximally relative to the core exposed at the distal portion of the optical fiber;
the determining determines that the irradiation target site is disposed in a direction perpendicular to a line segment connecting the first marker and the second marker in the acquired ultrasound image.

4. The phototherapy method according to claim 1, further comprising determining a positional relationship between the first marker and the irradiation target site in an acquired ultrasound image;
  wherein the first marker covers an entire outer circumference of the optical fiber.

5. The phototherapy method according to claim 1, further comprising:
  disposing the endoscope at a position in the digestive tract where the irradiation target site can be visualized, while observing the irradiation target site in a tomographic image of an organ adjacent to the digestive tract; and
  subsequent to the disposing, visualizing the irradiation target site.

6. The phototherapy method according to claim 5,
  wherein the digestive tract is a stomach or a duodenum;
  the irradiation target site is a cancer cell present in a pancreas; and
  the phototherapy method further comprises puncturing, with the needle tube, an inner wall of the stomach or the duodenum through to an inside of the pancreas.

7. The phototherapy method according to claim 5,
  wherein the digestive tract is a stomach;
  the irradiation target site is a cancer cell present in a stomach wall of the stomach; and
  the phototherapy method further comprises puncturing, with the needle tube, until a needle point of the needle tube is positioned inside the stomach wall.

8. The phototherapy method according to claim 1, wherein
  a second marker is provided proximally relative to the core exposed at the distal portion of the optical fiber; and
  the determining determines that the irradiation target site is disposed in a direction perpendicular to a line segment connecting the first marker and the second marker in an acquired ultrasound image;
  wherein the location is one of the first marker and the second marker.

9. The phototherapy method according to claim 8, wherein:
  the acquired ultrasound image including the irradiation target site; and
  the acquired ultrasound image including the irradiation target site, the first marker and the second marker.

10. The phototherapy method according to claim 8, wherein:
  the acquired ultrasound image including the irradiation target site; and
  the acquired ultrasound image including the line segment connecting the first marker and the second marker, and the line segment opposes the irradiation target site.

11. The phototherapy method according to claim 8, wherein:
  the acquired ultrasound image including the irradiation target site; and
  the acquired ultrasound image including the irradiation target site and the first marker.

12. The phototherapy method according to claim 8, wherein:
  the acquired ultrasound image including the irradiation target site; and
  the acquired ultrasound image including a line segment connecting the first marker and the distal end of the needle tube, and the line segment opposes the irradiation target site.

13. The phototherapy method according to claim 1, further comprising:
  subsequent to the advancing of the optical fiber, acquiring an ultrasound image including the irradiation target site; and
  the acquired ultrasound image including the irradiation target site and the needle tube.

14. The phototherapy method according to claim 1, further comprising:
  subsequent to the advancing of the optical fiber, acquiring an ultrasound image including the irradiation target site; and
  the acquired ultrasound image including a circumferential surface of the needle tube opposed to the irradiation target site.

15. The phototherapy method according to claim 1, wherein the endoscope is an ultrasound endoscope.

16. The phototherapy method according to claim 1, wherein the protective tube is one of white, transparent, or translucent.

17. The phototherapy method according to claim 1, wherein the first marker is provided distally relative to the core exposed at the distal portion of the optical fiber,
  wherein the protective tube covers the first marker.

18. The phototherapy method according to claim 17, further comprising a second marker provided on the optical fiber, and the second marker is provided proximally relative to the core exposed at the distal portion of the optical fiber, the protective tube covers the second marker.

19. The phototherapy method according to claim 1, wherein a space is provided between an inner surface of the protective tube and an outer surface of the core.

20. A phototherapy method comprising:
  introducing an endoscope into a digestive tract;
  while introducing the endoscope into the digestive tract, protruding a needle tube from a distal-end of the endoscope to puncture a vicinity of an irradiation target site with the needle tube;
  subsequent to the protruding, advancing the needle tube to the irradiation target site;
  during or after the protruding, advancing an optical fiber into at least a portion of the needle tube that is advanced to the irradiation target site;
  subsequent to the advancing of the optical, retracting the needle tube to expose light emitted from an outer circumferential surface of a portion of the optical fiber exposed from the needle tube to the irradiation target site; and
  subsequent to the retracting, and while maintaining a positional relationship between a location on the optical fiber exposed from the needle tube and a distal end of the needle tube, circumferentially radiating the light emitted from the portion of the optical fiber onto the irradiation target site;
  wherein the optical fiber has a core and a clad covering the core, the portion of the optical fiber comprises a circumferential surface of the core exposed at a distal portion of the optical fiber,
  the clad is provided proximally relative to the exposed circumferential surface of the core,
  a protective tube, other than the needle tube, is provided to cover the core exposed at the distal portion of the optical fiber,
  the advancing of the optical fiber comprises advancing at least the distal portion of the optical fiber having the exposed core and a corresponding portion of the protective tube into at least the portion of the needle tube, the retracting exposes at least the distal portion of the optical fiber having the exposed core and the corresponding portion of the protective tube,
a first marker provided on the optical fiber and the first marker is provided distally relative to the core exposed at the distal portion of the optical fiber,
a second marker provided on the optical fiber, and the second marker is provided proximally relative to the core exposed at the distal portion of the optical fiber, and
the protective tube covers the first marker, and the second marker.

\* \* \* \* \*